United States Patent [19]
Karell et al.

[11] Patent Number: 5,888,199
[45] Date of Patent: Mar. 30, 1999

[54] EAR CLEANING DEVICE WITH A FLEXION PART

[76] Inventors: Manuel L. Karell, 3573 22nd St.; David B. Smith, 1079 Church St., both of San Francisco, Calif. 94114

[21] Appl. No.: 999,345

[22] Filed: Dec. 29, 1997

[51] Int. Cl.$^6$ ....................................................... A61F 11/00
[52] U.S. Cl. .............................................................. 606/162
[58] Field of Search ...................... 606/162, 160, 606/172, 161; 30/123.3; 128/857, 864, 868

[56] References Cited

U.S. PATENT DOCUMENTS

| | | | |
|---|---|---|---|
| 651,395 | 6/1900 | Stapp | 606/162 |
| 2,617,409 | 11/1952 | Biederman | 606/162 |
| 5,209,757 | 5/1993 | Krug et al. | 606/162 |
| 5,334,212 | 8/1994 | Karell . | |
| 5,374,276 | 12/1994 | Lay . | |
| 5,509,921 | 4/1996 | Karell . | |
| 5,586,989 | 12/1996 | Bray, Jr. | 606/160 |
| 5,632,756 | 5/1997 | Kruglick . | |
| 5,715,850 | 2/1998 | Markgraaf | 606/162 X |

*Primary Examiner*—Michael Buiz
*Assistant Examiner*—Vikki Trinh

[57] ABSTRACT

A safer ear cleaning device having a stop to control depth of insertion, a blunted loop end for preventing perforation of the ear drum, a shaft with a flexing means and with a hole for irrigating wax.

17 Claims, 4 Drawing Sheets

EAR CLEANING DEVICE WITH A FLEXION PART

BACKGROUND OF INVENTION

1. Field of Invention

The instant invention relates generally to human and animal body tubular passage manipulators and more specifically it relates to a disposable ear cleaning device.

2. Description of Prior Art

Wax build up in an ear canal prevents adequate examination of the eardrum and may adversely affect hearing. A person may try to remove the wax, for example with a cotton swab, which tending to act as a plunger causes impaction or injury to the ear drum. To help prevent injury earwax cleaners (ear curette) were provided with depth control as in U.S. Pat. Nos. 5,334,212 and 5,509,921 to Karell, 1994 and 1996. U.S. Pat. No. 5,374,276 to Lay, 1994 and U.S. Pat. No. 5,632,756 to Kruglick, 1997, show ear cleaners combined with a swab.

SUMMARY OF THE INVENTION

An important goal of an ear cleaner is to prevent ear drum injury while providing ease of use for laypersons and professionals. What is needed and is presented in the instant invention, is a means for making the device safer while increasing the ability to remove the wax.

A primary object of the present invention is to provide an ear cleaning device that will overcome the shortcomings of the prior art devices. An ear wax cleaner, also known an ear curette, is composed of a shaft having two ends, one end connected to a handle, the other end connected to a wax extraction means. The curette end may have many configurations; however, in practice, the loop appears to be superior to the spoon, the hook, the cage, the swab and other configurations. Thus, a loop curette in which the end is blunted, and which flexes on contacting the ear drum accomplishes the safer goal. The instant invention provides a planar, substantially perpendicular surface at its tip. Also, the wax extraction end flexes at its point of connection; thus, on striking the ear drum (tympanic membrane), the cleaner end flexes on its shaft thereby moving away. Additionally, in the instant invention, the shaft is angled for increasing the sweep of rotation thus improving wax removal. A stop for controlling insertion depth is positioned on the shaft between its ends. Also, a means for locating which direction the curette faces is included.

An alternative configuration for the instant invention is an ear cleaner device with a shaft having a center hole for allowing liquid to traverse the shaft for irrigating out wax as the device is used. The liquid, for example water, may be manually pumped, such as with a bulb syringe, or may be mechanically pumped.

Also, the depth controlling means (stop) may be adjustable on the shaft for varying the length of penetration into the canal; or it may be fixed. If the depth controlling means is fixedly positioned, then a set of curettes having varying lengths may be utilized to remove wax from differently sized ear canals, for example, children.

A further object is to provide an ear cleaning device that is simple and easy to use.

A further object is to provide an ear cleaning device that may be used both for adult and child in different ethnic populations.

A further object is to have a stop or a shaft used as a handle.

A still further object is to provide a disposable ear cleaning device that is economical in cost to manufacture, using injection molding with plastic.

Further objects of the invention will appear as the description proceeds. To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF DRAWINGS

FIG 1A is a front view schematic drawing showing the general shape of the curette loop with blunted end.

FIG. 1B is a perspective top-down view schematic drawing showing the blunted end of the loop resting on the shaft above the stop.

FIGS. 2, 2A, are highly schematic drawings showing a shaft having a hole for liquid to traverse from end to end, and said shaft being inserted into a bulb syringe.

FIG. 2B is a magnified view of the hole exiting near the base of the loop extraction means.

DETAILED DESCRIPTION OF THE PRESENT INVENTION

Figure 1:
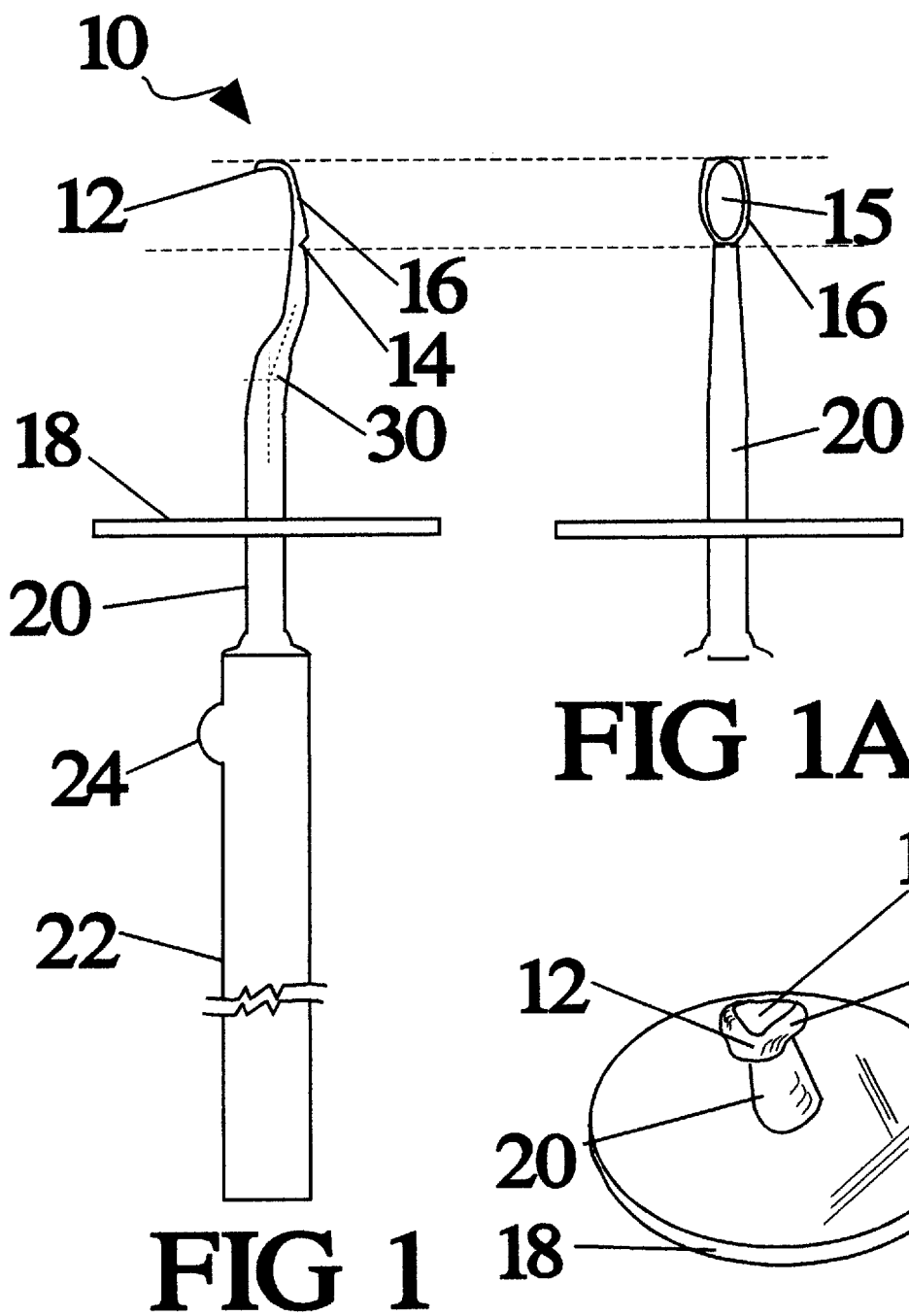
FIG. 1 is a side view schematic drawing showing a preferred configuration in which a loop curette has a blunt end, a flexion means, a shaft with an off-center angle, a depth controlling (stop) means, a handle, and a locating means (an elevation).
Figure 2:
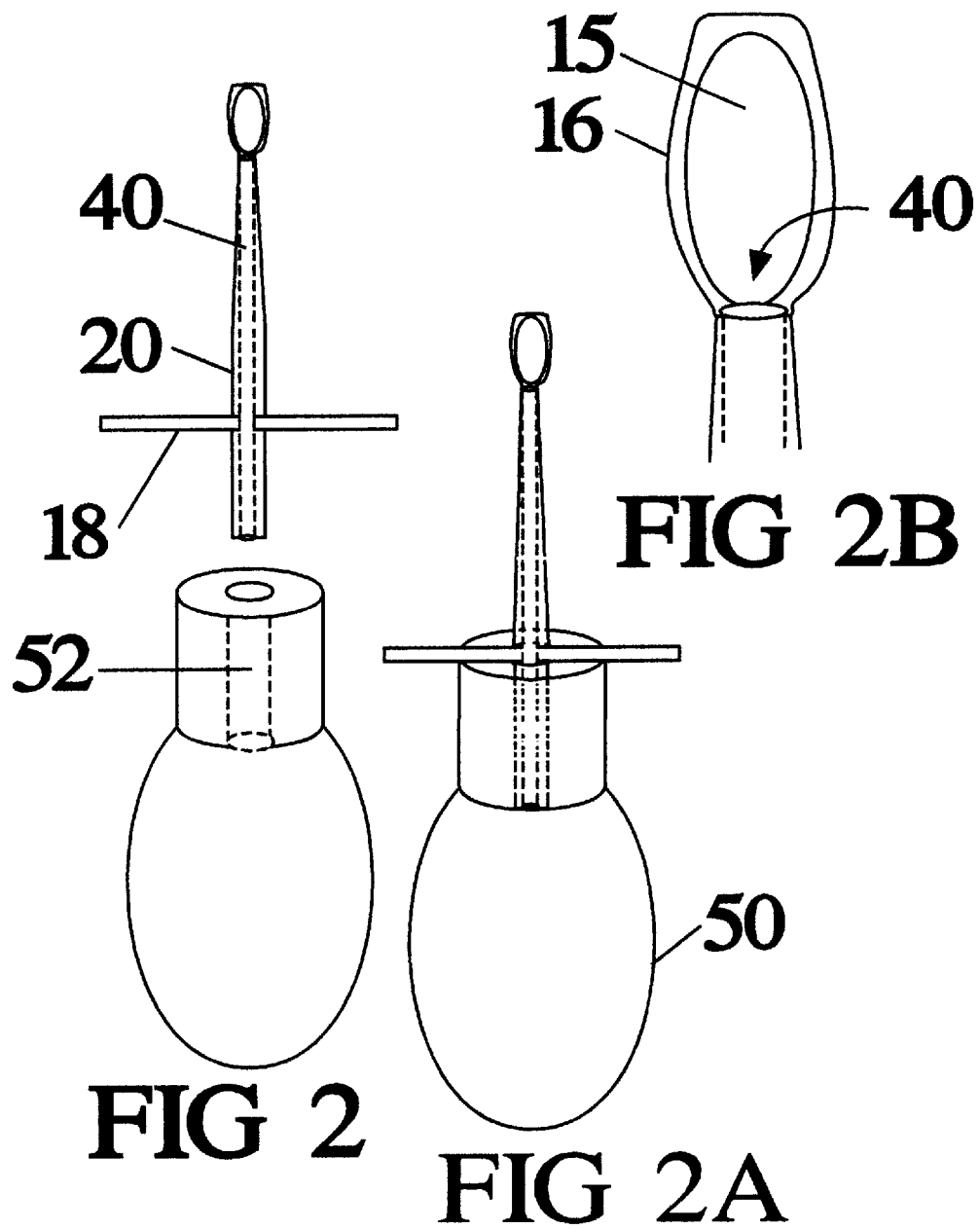
Figure 3:
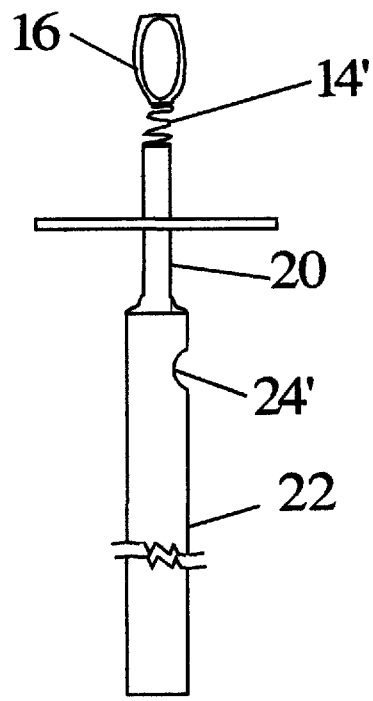
FIG. 3 is a schematic drawing showing a locating means being a depression rather than an elevation, and a flexion means configured as a spring means.

The instant invention is best visualized in drawings, FIGS. 1–3. In FIG. 1, the instant invention(10) comprises a shaft(20) having two ends, one end having a handle means (22) and the other end having a wax extraction means(16). A depth controlling (stop) means(18) is placed between said two ends. In its preferred embodiment, the wax extraction means(16) comprises a loop(15) having a puncture preventing means(12) placed at its distal portion and being substantially perpendicular to said loop(15). At the base of said wax extraction means(16) is a flexion means(14), which allows the wax extraction means to flex in relation to the shaft(20) on contacting an ear drum. The shaft(20) further comprises an off-center angle means(30), which provides for an increased sweep as the handle(20) is rotated on its axis during wax removal. FIGS. 1 and 1A show the blunt nature of the wax extraction means(16). FIG. 1B is a top-down perspective view showing loop(15) resting on shaft(20) and ending bluntly in puncture preventing means(12). Handle (22) additionally comprises an elevated locating means(24). FIG. 3 shows an alternative depressed locating means(24'). The locating means(24) indicates to the user which direction the loop(15) is facing. FIG. 3 also shows an alternative flexion means(14') configured as a spring. An alternative configuration depicted in FIGS. 2 and 2A show a shaft(20) additionally comprising a hole(40) which allows liquid to traverse end to end, for example, propelled by a bulb syringe(50). The shaft(20) is inserted into the orifice(52) of the bulb, and positioned against the depth controlling means (18); thus the bulb syringe is acting as a handle. FIG. 2B is an enlarged view showing shaft hole(40) exiting near base of loop(15).

Figure 3A:
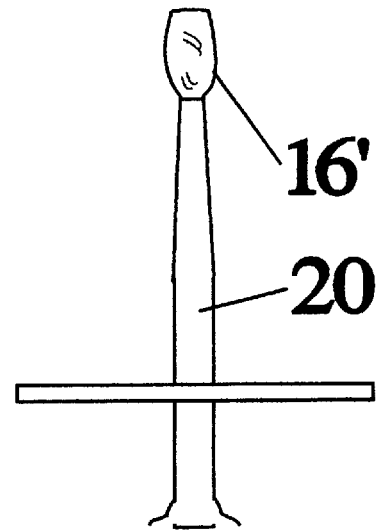
FIG. 3A is an extraction means being configured as a spoon.
Figure 3C:
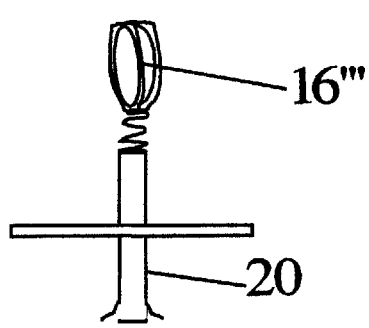
FIG. 3C is an extraction means being configured as multiple loops.
Figure 3B:
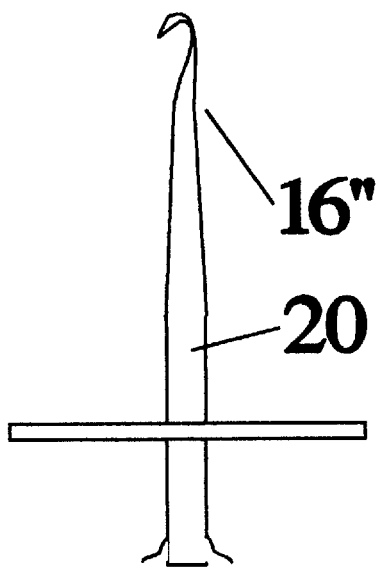
FIG. 3B is an extraction means being configured as a hook.

FIGS. 3A, 3B, 3C are representations of the wax extraction means being a spoon(16') or a hook(16"), or configured as multiple loops(16''').

Figure 4:
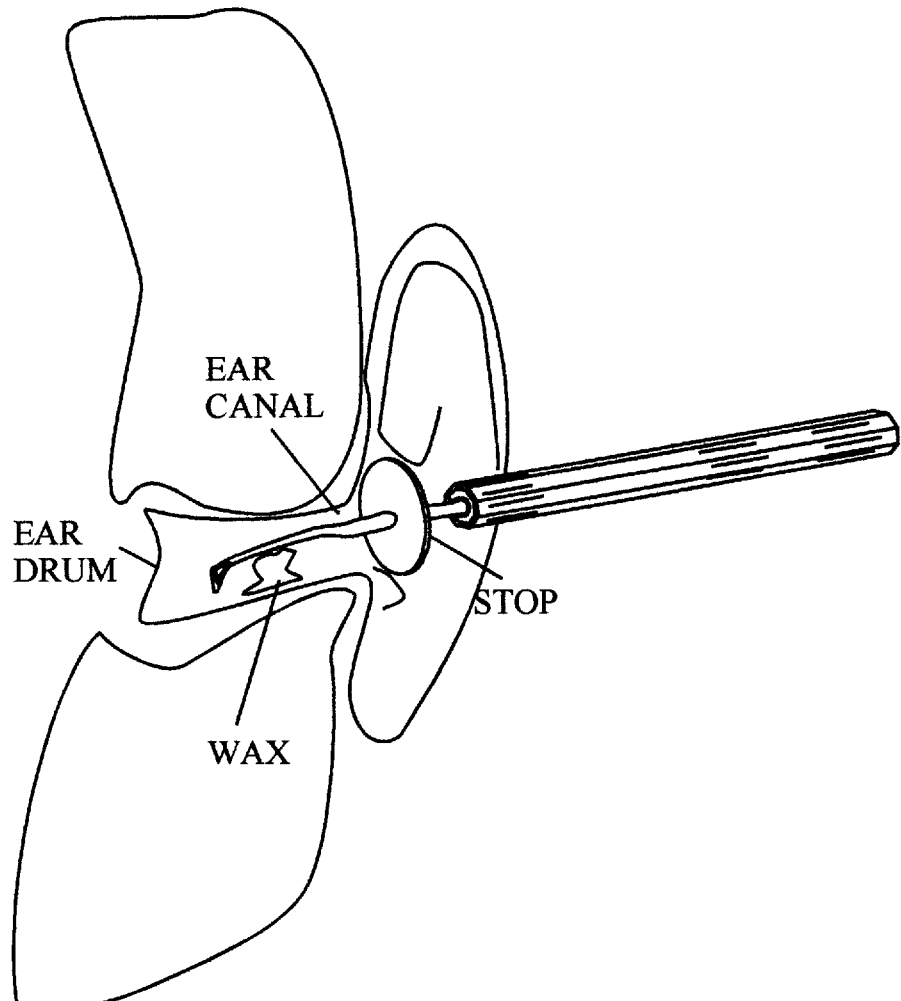
FIG. 4 is a highly schematic drawing showing a curette in use within an ear canal.

FIG. 4 is a schematic representation of the instant invention(10) in use for removing wax, wherein the depth controlling means(18) rests external to ear canal.

We claim:

1. An ear cleaning device comprising:
   a shaft having a proximal end and a distal end;
   an extraction means for engaging, capturing and extracting wax located in an ear canal of a person or an animal, said extraction means located at the distal end of the shaft;
   a handle mounted to the proximal end of the shaft for grasping and rotating the device;
   an adjustable depth controlling means slidably mounted onto the shaft for varying the length of penetration into the canal; aid
   wherein the shaft includes a flexion means associated with the extraction means for allowing the extraction means to flex relative to the shaft when contacting an e drum so as to prevent injury.

2. The device as recited in claim 1, wherein the extraction means comprises a puncture preventing means which is planar and substantially perpendicular to said extraction means for preventing perforation of the ear drum.

3. The device as recited in claim 1, wherein said shaft additionally has an off-center angle means for providing an angle off center to axis of rotation for increasing sweep radius of said extraction means.

4. The device as recited in claim 1, wherein the shaft further comprises a hole means traversing from the distal end to the proximal end for allowing a liquid to pass for irrigating wax from the ear canal while said extraction means is utilized.

5. The device as recited in claim 1, wherein said handle additionally comprises a locating means for locating which direction said extraction means is facing.

6. The device as recited in claim 5, wherein said locating means is an elevation.

7. The device as recited in claim 5, wherein said locating means is a depression.

8. The device as recited in claim 1, wherein the extraction means further comprises a set of curettes having fixed depth controlling means sized and configured to fit varied ear canal lengths.

9. The device as recited in claim 1, wherein said flexion means is a wedge-shape concavity means for reducing thickness of said shaft for allowing said shaft to flex at this point.

10. The device as recited in claim 1, wherein said flexion means is a spring means for allowing said shaft to flex at this point.

11. The device as recited in claim 1, wherein said extraction means is a loop.

12. The device as recited in claim 1, wherein said extraction means is multiple loops.

13. The device as recited in claim 1, wherein said extraction means is a spoon.

14. The device as recited in claim 1, wherein said extraction means is a hook.

15. An ear cleaning device comprising:
    a shaft having a proximal end and a distal end;
    an extraction means for engaging, capturing and extracting wax located in an ear canal of a person or an animal, said extraction means located at the distal end of the shaft;
    wherein said extraction means includes a set of curettes having fixed depth controlling means sized and configured to fit varied ear canal lengths;
    a handle mounted to the proximal end of the shaft for grasping and rotating the device;
    wherein the shaft includes a flexion means associated with the extraction means for allowing the extraction means to flex relative to the shaft when contacting an ear drum so as to prevent injury; and
    wherein the shaft further comprises a hole means traversed from the distal end to the proximal end for allowing a liquid to pass for irrigating wax from the ear canal while said extraction means is utilized.

16. The device as recited in claim 15, wherein the flexion means is a spring means for allowing the shaft to flex.

17. The device as recited in claim 15, wherein the device further comprises an adjustable depth controlling means slidably mounted on the shaft for controlling the depth of insertion of the extraction means.

* * * * *